US009486268B2

(12) United States Patent
Bennett et al.

(10) Patent No.: US 9,486,268 B2
(45) Date of Patent: Nov. 8, 2016

(54) BATTERY PACK ATTACHED TO A CABLE

(71) Applicant: GYRUS ACMI, INC., Southborough, MA (US)

(72) Inventors: Michael J. Bennett, Bartlett, TN (US); Phillip A. Ryan, Memphis, TN (US); Paul E. Yarbrough, Stanton, TN (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 14/802,109

(22) Filed: Jul. 17, 2015

(65) Prior Publication Data

US 2015/0320474 A1 Nov. 12, 2015

Related U.S. Application Data

(62) Division of application No. 14/012,250, filed on Aug. 28, 2013, now Pat. No. 9,118,057.

(60) Provisional application No. 61/694,522, filed on Aug. 29, 2012.

(51) Int. Cl.
*A61B 18/04* (2006.01)
*H01M 2/10* (2006.01)
*H01M 2/34* (2006.01)
*H05K 5/00* (2006.01)
(Continued)

(52) U.S. Cl.
CPC ......... *A61B 18/04* (2013.01); *A61B 17/32002* (2013.01); *A61B 18/00* (2013.01); *A61B 18/148* (2013.01); *H01M 2/1022* (2013.01); *H01M 2/34* (2013.01); *H05K 5/0086* (2013.01); *A61B 17/26* (2013.01); *A61B 2017/0023* (2013.01); *A61B 2017/00734* (2013.01); *A61B 2018/00571* (2013.01); *A61B 2217/007* (2013.01); *A61B 2218/002* (2013.01); *H01M 2220/30* (2013.01)

(58) Field of Classification Search
CPC ............ A61B 2018/00178; A61B 2018/1412; A61B 2018/00184; A61B 2018/1226; A61B 2018/00029; A61B 2018/00208; A61B 2217/007; H05K 5/0086
USPC ...................................... 606/41, 45
See application file for complete search history.

(56) References Cited

U.S. PATENT DOCUMENTS 5,112,299 A 5/1992 Pascaloff
5,814,044 A 9/1998 Hooven
(Continued)

FOREIGN PATENT DOCUMENTS

DE 2136749 A1 2/1973
WO 99/03186 A1 1/1999
(Continued)

OTHER PUBLICATIONS

PCT Search Report and Written Opinion dated Nov. 26, 2013; Application No. PCT/US2013/057043.

*Primary Examiner* — Michael Peffley
*Assistant Examiner* — Thomas Giuliani
(74) *Attorney, Agent, or Firm* — The Dobrusin Law Firm, P.C.

(57) ABSTRACT

An article comprising: (i) a handheld device including (a) a housing, (b) a powered element within the housing; (ii) a battery pack, wherein the handheld device is connected by an external cable to a functional system, wherein the battery pack is attached to the external cable, and wherein the battery pack supplies power to the powered element.

20 Claims, 4 Drawing Sheets

(51) Int. Cl.
*A61B 17/32* (2006.01)
*A61B 18/14* (2006.01)
*A61B 18/00* (2006.01)
*A61B 17/00* (2006.01)
*A61B 17/26* (2006.01)

(56) References Cited

U.S. PATENT DOCUMENTS

| | | | |
|---|---|---|---|
| 6,017,354 A * | 1/2000 | Culp | A61B 90/98 604/22 |
| 7,879,032 B1 | 2/2011 | Garito et al. | |
| 2003/0149424 A1 | 8/2003 | Barlev et al. | |
| 2004/0092992 A1 * | 5/2004 | Adams | A61B 17/26 606/180 |
| 2007/0093868 A1 | 4/2007 | Fugo | |
| 2008/0065001 A1 | 3/2008 | DiNucci et al. | |
| 2010/0198009 A1 | 8/2010 | Farr et al. | |
| 2012/0265278 A1 * | 10/2012 | Fourkas | A61B 18/02 607/105 |

FOREIGN PATENT DOCUMENTS

| | | |
|---|---|---|
| WO | 2010/075438 A1 | 7/2001 |
| WO | 2011/141752 A2 | 11/2011 |

* cited by examiner

BATTERY PACK ATTACHED TO A CABLE

RELATED APPLICATIONS

This application is a divisional application claiming priority to and the benefit of U.S. patent application Ser. No. 14/012,250, filed on Aug. 28, 2013, granted as U.S. Pat. No. 9,118,057, entitled "Battery Pack Attached to a Cable", which claims the benefit and priority to U.S. Provisional Application No. 61/694,522, filed on Aug. 29, 2012, the contents of which are both hereby incorporated by reference as if recited in full herein for all purposes.

FIELD

The present invention relates generally to power sources for hand-held devices, and more particularly a battery pack supplying energy to a motor of an electrosurgical hand-held medical device.

BACKGROUND

Different versions of battery packs supplying energy to hand-held devices are known, for example U.S. Pat. Nos. 5,112,299; 5,814,044; or U.S. Patent Applications Nos. 2004/0092992 and U.S. 2008/0065001, all of which are expressly incorporated by reference in their entirety herein for all purposes. When operating a hand-held device, a user may want to manipulate a light-weight device. This is especially imperative when a user operates the device for prolonged time, such as a surgeon operating a medical hand-held device utilized during surgery. The problem is that such devices have batteries located in their housing; therefore adding weight to the housing, thus adding extra weight a surgeon has to hold in his or her hand while operating the device.

Additionally, a user of a hand-held device powered by a battery pack located outside of the housing may want to keep the battery pack in a certain distance and away from the floor or other surfaces, such as a surgeon may need to ensure that the battery pack does not compromise the sterile environment around a patient in the operating room. Therefore, the user of the device may want the battery pack to be lightweight, portable, and remote from the device. The problem is that the known battery packs located outside of the housing supplying energy to hand-held devices are bulky as they house additional mechanisms, such as a recharging mechanism, which requires setting of the battery pack on the floor or other surface which may compromise sterility around the patient.

Further still, a user of a hand-held device, such as an electrosurgical hand-held device, powered by a battery pack located outside of the housing may need to connect the hand-held device to a functional system, such as a generator or an irrigation device. Therefore, if a user needs to connect the device to a generator or an irrigation system, a cable containing electrosurgical lead wires or an irrigation line leading from the device to a generator or an irrigation system is needed.

Therefore, there is need for a battery pack supplying energy to a functioning portion of a hand-held device which would be located outside of the device's housing; thus reducing weight of the hand-held portion of the device. Additionally, there is a need for a battery pack remote from the device which would allow a user of the device to keep the sterile environment around a patient in the operating room. Finally, there is a need for a system utilizing a battery pack which transmits electrical energy from the battery pack to the handpiece, and such a system also allows a user of the device to connect the handpiece to another functioning system, such as a generator or an irrigation system.

SUMMARY

An article comprising: (i) a handheld device including (a) a housing, (b) a powered element within the housing; (ii) a battery pack, wherein the handheld device is connected by an external cable to a functional system, wherein the battery pack is attached to the external cable, and wherein the battery pack supplies power to the powered element.

Another embodiment includes: an article comprising: (i) an electrosurgical medical device including (a) a housing, (b) a powered element within the housing; (ii) a battery pack, wherein the electrosurgical medical device is connected by an external cable to a functional system in a console, wherein the battery pack is attached to a segment of the external cable connecting the housing to the battery pack, and wherein the battery pack supplies power to the powered element.

Another embodiment includes: an article comprising: (i) an electrosurgical medical device including (a) a housing, (b) a motor within the housing; (ii) a battery pack, wherein the electrosurgical medical device is a debrider with at least one inner blade coupled to the motor, wherein the electrosurgical medical device is connected by an external cable to a generator, wherein the battery pack is attached to a segment of the external cable connecting the housing to the battery pack, wherein the battery pack is attached to a plug interfacing with the generator by another segment of the external cable, wherein the battery pack supplies power to the motor, and wherein the battery pack is wired to the external cable.

Preferably, the functional system is located in a console. Preferably, the handheld device is an electrosurgical medical device. Preferably, the electrosurgical medical device is a debrider. Preferably, the console houses a generator, and the external cable contains battery lead wires and electrosurgical lead wires. Preferably, a segment of the external cable connects the battery pack to a plug interfacing with the generator. Preferably, the electrosurgical medical device has at least one electrode, and the generator supplies power to the at least one electrode. Preferably, the electrosurgical medical device has at least one inner blade coupled to the motor. Preferably, a segment of the external cable is an irrigation line and the console is an irrigation system.

The present teachings provide a battery pack attached to a cable and a method of using a battery pack attached to a cable supplying electrical energy to a hand-held device. The advantage of the present invention is the placement of the battery pack outside of the housing of a hand-held device; therefore allowing for weight-reduction of the device's housing which makes manipulation and operation of the device more comfortable for a user. An additional advantage of the present invention is that the battery pack is attached to an external cable leading from the device to another functional system; therefore allowing for spacing the battery pack away from the device without having to place the battery pack on the floor or other surfaces, thus preventing corruption of the sterile environment around a patient in the operating room. Further advantage of the present invention lies in utilization of an external cable leading from the device to another functioning system, such as a generator. Therefore, a user may connect the device to the functioning system with the same cable which is being used to carry the battery pack, thus preventing a need to add additional cables which contributes to user's safety.

DETAILED DESCRIPTION

Figure 1:
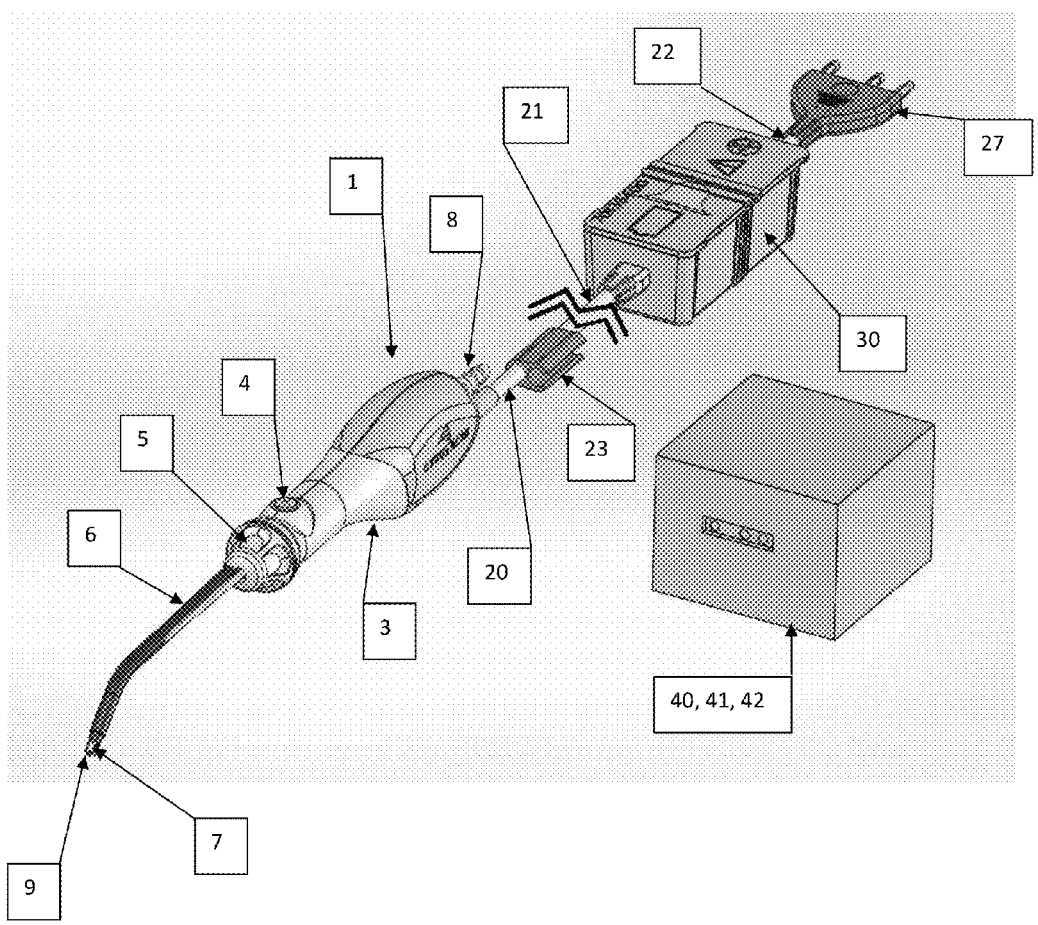
FIG. 1 illustrates one example of an article including a battery pack of the teachings herein attached to device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosure of all articles and references, including patent applications and publications, are incorporated by reference for all purposes. Other combinations are also possible as will be gleaned from the following claims, which are also hereby incorporated by reference into this written description.

The present teachings provide a battery pack attached to an external cable supplying energy to a device, such as a hand-held medical device, a hand-held irrigator, and the like. A hand-held medical device may be for example an electrosurgical debrider, such as a tonsil and adenoid debrider. Preferably, the device has a hand-held portion wherein power is provided to the functioning portion of the device by one or more batteries of the battery pack. More preferably, the device is a light-weight, portable hand-held device. The device may comprise a housing, a handle, a powered element, a motor, a light, a light-emitting diode (LED), a circuit, a motor within the housing powered by one or more batteries in the battery pack, motor lead wires, electrosurgical lead wires, radiofrequency lead wires, camera lead wires, optical fibers, an optical end, a camera, an LED activation light, a cable, an external cable leading from the device to a functional system housed in a console, an attachment on the external cable, a port, an irrigation port, a suction port, tubing, irrigation tubing, suction tubing, a suction tip, a rotating nose cone, a rotating inner blade placed within an external tube, a shaver blade, one or more electrodes, controls for the device, a switch for establishing a contact between battery contacts and battery lead wires, and the like.

The housing accommodates working components used to operate the device. The housing can be any structure that performs this function. The housing may have any size, shape, configuration, or a combination thereof so that the housing can be gripped with a left hand, right hand, or both. Preferably, the housing has an ergonomic shape. The housing may be made of any material commonly utilized in housings of devices, such as plastic, metal, or the like. Preferably, the housing is made of a lightweight material. Preferably, the housing is made of an engineering plastic, more preferably acrylonitrile butadiene styrene (ABS), polycarbonate (PC), or a blend of ABS and PC. The housing may have an elastomer grip for better gripping and comfort. The housing may further contain a plurality of controllers, various parts of the controllers' mechanism, the like, or a combination thereof. For example, the housing may contain a shaft with different endings, such as a malleable inner shaving blade, a cutter, a distal suction hole/tip; electrodes, such as a monopolar electrosurgical coagulation electrode to which energy is supplied from a generator; different types of connections, such as a suction connection or an irrigation connection; an LED light activation button; a powered element; a motor; a light; an LED; a circuit; a motor power switch, an optical end, a camera, and the like. The housing may be connected to a functional system in a console by an external cable. Preferably, a battery pack attached to the external cable by which the housing is connected to a functional system in a console supplies electrical energy to the powered element within the housing.

The powered element receives electrical energy from the one or more batteries and powers different mechanisms of the device. The powered element can be a motor, a light, an LED, a circuit, and the like. Preferably, the powered element is reliable, cost-effective, power efficient, light-weight, quiet, and long-lived. Preferably, the powered element can withstand a variety of environmental conditions to which devices used in the invention may be exposed to, for example caustic fluids, radiation, steam, varying temperatures, vacuum, and/or physical abuse. The powered element can contain plastic, metal, glass, and/or engineered ceramics components. Preferably, the powered element is made of a lightweight material. Preferably, the powered element is a motor. The motor turns electrical energy into mechanical work and powers different mechanisms of the device. The motor can be a coreless motor or have an iron-core. Preferably, the motor is a direct current (DC) motor. The DC motor can be a brushless type or a brush type motor with precious-metal brush system, carbon-brush system, or the like. The motor can be turned on and off with a motor power switch. The motor power switch can be located anywhere on the housing, such as along the top edge of the device, and the like. The one or more batteries within the battery pack supply electrical energy to the powered element. The powered element is placed within the housing. The powered element powers mechanisms of the device, such as an inner blade on the device's shaft.

The housing may be connected to a functional system and the battery pack with an external cable. The external cable may transmit a low-frequency signal, high-frequency signal, light, irrigation fluids, or any other material the device needs to function from the functional system to the housing and electrical power from the battery pack to the housing.

The cable may have any size, material, shape, type, configuration, or a combination thereof. Preferably, the external cable has sufficient length to connect the battery pack to the housing while giving a user the option to keep the battery pack away from the workplace, such as to keep a sterile environment around a patient. The external cable may use copper, aluminum, solid conductors, optical fibers, plastic, and the like. The cable is insulated. Preferably, the cable is flexible so that it can be wound and repeatedly moved. Preferably, the battery pack is attached to the cable. More preferably, the battery pack is wired to the cable. Even more preferably, the battery pack is attached and/or wired to the cable in such a distance from the housing that a user may use the housing without compromising the sterile environment around a patient. The cable may comprise a plurality of segments, such as a segment connecting the housing to the battery pack and a segment connecting the battery pack to a functional system. Preferably, the cable has a segment connecting the housing with the battery pack containing electrosurgical lead wires and battery lead wires and a second segment connecting the battery pack with a functional system within a console, such as a generator, containing electrosurgical lead wires only. More preferably, the second segment connects the battery pack to a plug interfacing the generator. Alternatively, the cable may have a segment connecting the housing with the battery pack containing battery lead wires and an irrigation line and a second segment connecting the battery pack with a functional system within a console, such as an irrigation system, containing irrigation line only. Alternatively, the cable may have a segment connecting an optical end within the housing with the battery pack containing battery lead wires and optical fibers and a second segment, connecting the battery pack with a functional system within a console, such as a light source or a camera, containing optical fibers only. Alternatively, the cable may have a segment connecting a camera within the housing with the battery pack containing battery lead wires and camera lead wires and a second segment, connecting the battery pack with a functional system, such as a video displayer, with the camera lead wires only. The cable may be plugged or hardwired to a functional system. The external cable may contain a plurality of attachments. Preferably, the external cable contains a clip for attaching additional tubing, such as a suction hose clip which allows for suction tubing to be kept safely out of the user's way.

The battery lead wires provide transmission of electrical energy between the batteries and the device. The battery lead wires may have any size, shape, configuration, or a combination thereof. The battery lead wires are made of any material which is typically utilized in battery lead wires. Preferably, the battery lead wires are made of a material capable of transmitting electric energy from the battery contacts to the device. Preferably, the battery lead wires are flexible, corrosion resistant, and capable of wet applications. The battery lead wires lead from one or more contacts of the one or more batteries in the battery pack to the functioning system of the housing, such as a powered element. The battery lead wires may be attached to the outside of the external cable or be placed inside of the external cable. Preferably, the battery lead wires are attached to or placed within the segment of the external cable connecting the housing with the battery pack.

The electrosurgical lead wires provide transmission of a high-frequency signal between a generator and the device. The electrosurgical lead wires may have any size, shape, configuration, or a combination thereof. The electrosurgical lead wires are made of any material which is typically utilized in electrosurgical lead wires. Preferably, the electrosurgical lead wires are made of a material capable of transmitting high-frequency signal from a generator to the device. Preferably, the electrosurgical lead wires are flexible, corrosion resistant, and capable of wet applications. The electrosurgical lead wires are disposed in or are attached to the external cable leading from the housing to the generator. Preferably, the electrosurgical lead wires are in the segment of the external cable connecting the housing with the battery pack and in the segment of the external cable connecting the battery pack with the generator. Preferably, the electrosurgical lead wires are radiofrequency lead wires providing transmission of a radiofrequency signal between a generator and the device.

The irrigation line provides transmission of a fluid between an irrigation system to a housing of the device. The irrigation line may have any size, shape, configuration, or a combination thereof. The irrigation line is made of any material which is typically utilized in irrigation lines of medical devices, such as silicone. Preferably, the irrigation line is made of a material capable of carrying fluids assisting in washing out or flushing a wound or body opening, such as water, saline, aminoacetic acid, antiseptic solution, or the like from an irrigation system to the device. The irrigation line may be flexible, corrosion resistant, sterile, latex-free, long-lasting, for multiple patient use, any combination thereof, and the like. The irrigation line may contain a back-flow valve assuring infection prevention. The irrigation line may be connected to an irrigation mechanism or an irrigation port in the housing.

The optical fibers provide transmission of light between a light source or a camera within a console to an optical end within the device. The optical fibers may have any size, shape, configuration, or a combination thereof. The optical fibers are made of any material which is typically utilized in optical fiber cables, such as transparent high quality extruded glass or plastic. Preferably, the optical fibers are made of a flexible material capable of carrying light through the external cable to the optical end within the housing of the device. The optical fibers may be flexible; single- or multi-mode; coated with plastic layers in a protective tube; arranged into an optical fiber cable, and each end of the optical fiber cable may be terminated with a connector so that a user can easily connect the optical fiber cable to the optical end within the housing and the camera or a light source within the console.

The camera lead wires provide transmission of electricity between a video displayer within a console to a camera within the device. The camera lead wires may have any size, shape, configuration, or a combination thereof. The camera lead wires are made of any material which is typically utilized in camera lead wires. Preferably, the camera lead wires are made of a material capable of transmitting electric energy from the video displayer to the camera within the device. Preferably, the camera lead wires are flexible, corrosion resistant, and capable of wet applications.

The functioning system enables the device to carry out a function the device is designed to do. Preferably, the device is a medical device and the functioning system allows the medical device to carry out a function the medical device is designed to do. For example, a console may house the functioning system. The console may be any structure housing a mechanism, such as a generator, an irrigation system, a light source, a camera, a video displayer, and the like. The console may have any size, shape, configuration, or a combination thereof. The console may be made of any material commonly utilized in consoles for devices. Preferably, the console withstands a variety of environmental conditions to which devices used in the invention may be exposed to, for example caustic fluids, radiation, steam, varying temperatures, vacuum, and/or physical abuse.

The console may house a generator. The generator converts mechanical energy to electrical energy which is supplied to one or more electrodes of the device. The generator may be a monopolar radio frequency generator. The generator may have different settings, produce different waveforms, produce a continuous single frequency wave, create a repetitive waveform, provide sophisticated waveforms with power adjusted in real time, and the like. The generator may have various types of analog modulation, such as AM, FM, phase modulation, and pulse modulation. The generator may have a built-in attenuator allowing a user to vary the signal's output power, thus accommodating a user's need for different amount of signal power for different applications. Preferably, the generator is a standard monopolar generator with a 3-prong plug connection. The generator is connected to the housing with electrosurgical lead wires placed in the external cable.

Alternatively, the console may house an irrigation system. The irrigation system supplies a fluid to the housing of the device including an irrigation mechanism. The irrigation system may be any structure performing this function. Preferably, the irrigation system has sufficient flow of the fluid to meet a plurality of applications. The irrigation system may supply one or more irrigation fluids, such as water, saline, aminoacetic acid, antiseptic solution, and the like. The irrigation system may comprise a multi-application pump, flow controls, pressure display, and the like. The irrigation system is connected to the housing with an irrigation line placed disposed in or connected to the external cable.

The battery pack holds, secures, and protects batteries which supply electrical energy to the powered element in the housing of the device. The battery pack may have any size, shape, configuration, or a combination thereof. The battery pack may be made of any material with low electrical conductivity commonly utilized in battery packs for devices. Preferably, the material is also lightweight. More preferably, the material withstands a variety of environmental conditions to which devices used in the invention may be exposed to, for example caustic fluids, radiation, steam, varying temperatures, vacuum, and/or physical abuse. The battery pack may further contain an elastic member which may be applied over the battery pack to further protect it from external exposure. The battery pack may also contain a crude splash resistant sealing to prevent the battery pack against fluids. The battery pack is located outside of the housing. Preferably, the battery pack is attached and/or wired to an external cable. More preferably, the battery pack is attached and/or wired to an external cable leading from the housing to a functional system. Preferably, if the device is a medical device, the battery pack is attached to the external cable at a certain distance, away from the medical device, to keep the sterile environment around a patient. The battery pack may comprise a battery support (a base), an opposing battery support (a cover), one or more batteries, battery lead wires, electrosurgical lead wires, an irrigation line, and the like. Various parts of the battery pack, such as the battery support, the opposing battery support, or the like may contain signage, such as "ON," "OFF," arrows, or the like to offer a user visual affirmation that electricity is being transmitted from the battery pack to the device.

The one or more batteries provide electrical energy to the device, specifically to the powered element of the device. The one or more batteries may be any size, shape, configuration, or a combination thereof so that they securely fit within the opposing battery support's battery compartment and supply sufficient amount of energy to the device. The one or more batteries may be any shape, such as round, not round, flat or square. The one or more batteries may be made of any material typically utilized in batteries of devices, such as various metals, such as zinc-carbon, zinc-chloride, zinc-manganese, nickel oxyhydroxide, nickel-cadmium, nickel-zinc, lithium, or the like, carbon, or polymers. The one or more batteries may be any type typically utilized in devices, such as triple-A batteries, double-A batteries, 9-Volt batteries, 4.5-Volt batteries, D batteries, C batteries, and the like. The one or more batteries may be rechargeable or non-rechargeable. The one or more batteries may be disposable and/or recyclable. The batteries may be in a plurality of positions. Preferably, the batteries may be in an non-engaged position, a ready-to-be-engaged position, and an engaged position. When the batteries are in the non-engaged position, the battery contacts are not in contact with the battery lead wires. In the ready-to-be engaged position, the battery contacts are positioned to be in contact with the battery lead wires but transmission of electricity is prevented, for example by an activation tab spaced between the battery contacts and the battery lead wires. When the batteries are in the engaged position, the battery contacts are in contact with the battery lead wires and electricity is being transmitted from the batteries to the device. Preferably, the battery contacts are not in contact with the battery lead wires and/or terminals until a user is ready to use the device. A user can establish a contact between the battery contacts and the battery lead wires by inserting batteries into the battery pack, by removing an activation tab and/or placing the batteries in the engaged position, by turning a switch, and the like. The one or more batteries are placed within the battery pack and connected to the device by battery lead wires which are in contact with one or more battery contacts in the battery pack and the powered element in the housing.

In a preferred embodiment, the housing may contain an LED activation light indicating a contact has been established between the battery lead wires and the battery contacts and that electrical energy is being supplied to the powered element of the device by getting illuminated. The LED activation light can be anything that performs this function. The LED activation light may have any size, material, shape, type, configuration, or a combination thereof. The LED activation light can be placed anywhere within or on the housing. Preferably, the LED activation light is placed on the housing in such a way that a user can see the LED activation light while holding and operating the device and is alerted when the light illuminates.

To operate the invention, a user can activate the battery pack by inserting one or more batteries into the battery pack, removing an optional activation tab preventing transmission of electricity between battery contacts and the battery lead wires, or setting the batteries into an engaged position when electrical energy is being transmitted from the batteries to the powered element within the housing of the device. A user can check that electricity is being transmitted by seeing the LED activation light illuminated. A user can connect the device by the attached external cable to the functional system housed within a console. If a user is utilizing an electrosurgical device, a user can plug the external cable's segment carrying electrosurgical lead wires ending with a plug into the generator. Alternatively, a user may connect the external cable's segment carrying irrigation line to an irrigation system. Alternatively, a user may connect the external cable's segment carrying the optical fibers to a light source of a camera. Alternatively, a user may connect the external cable's segment carrying camera lead wires to a video displayer. Alternatively, the hand-held device may be hardwired to the console. A user may also connect suction or other tubing to a port on the housing and attach the tubing into the clip attached to the external cable.

FIG. 1 illustrates one example of an article including a battery pack (30) attached to a hand-held device (1). The device (1) is an electrosurgical medical device (1), a debrider (1). As illustrated, the debrider (1) comprises a housing (3) including a powered element (2) (not depicted), a rotating nose cone (5), an external tube (6) containing an inner blade (7), an electrode (9), a port (8) to be connected to a tubing, such as a suction port to be connected to a suction tubing, and an LED activation light (4) indicating transmission of electricity from the battery pack (30) to the device (1). The device (1) can be connected to a functional system (40) disposed within a console (41) with an external cable (20). The functional system (40) is a generator (42). As illustrated, the external cable (20) comprises a segment (21) connecting the housing (3) to the battery pack (30) attached to the cable (20) and a segment (22) capable of connecting the battery pack (30) to the console (41). The segment (22) contains a monopolar three-prong plug (27) ready to be plugged into the functional system (40). The external cable (20) further includes a clip (23) for attachment of tubing to the external cable (20).

Figure 2:
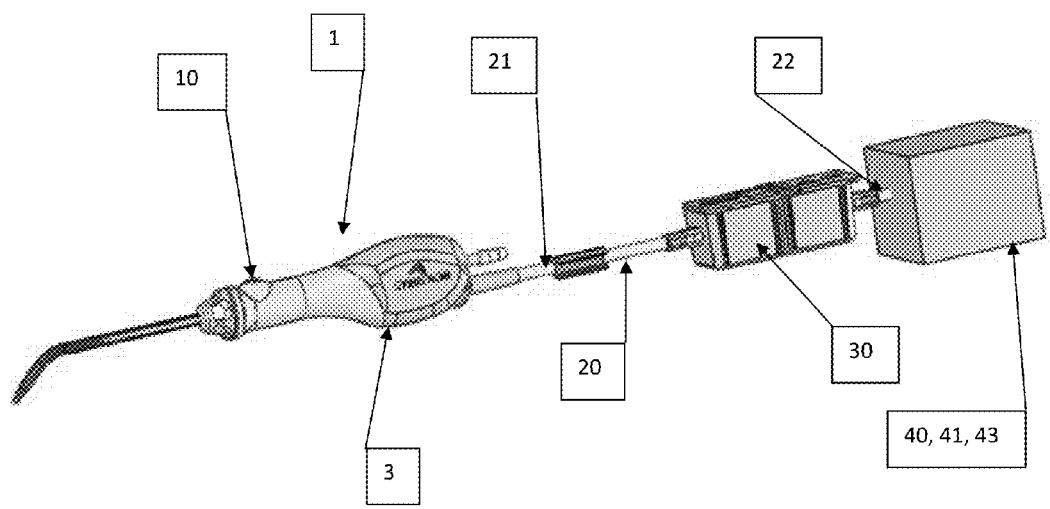
FIG. 2 illustrates another example of an article including a battery pack of the teachings herein attached to a device.

FIG. 2 illustrates another example of an article including a battery pack (30) of the teachings herein attached to a device (1). The device (1) is an electrosurgical medical device (1), a debrider (1). As illustrated, the debrider (1) is hardwired to a functional system (40) housed within a console (41) with an external cable (20). The functional system is an irrigation system (43). A powered element (2) (not depicted) is a motor (11) (not depicted) powered by the battery pack (30). A motor power switch (10) for turning the motor on and off is located on top of the housing (3). As illustrated, the external cable (20) comprises a segment (21) connecting the housing (3) of the device (1) to the battery pack (30) and a segment (22) connecting the battery pack (30) to the functional system (40) housed within the console (41).

Figure 3:
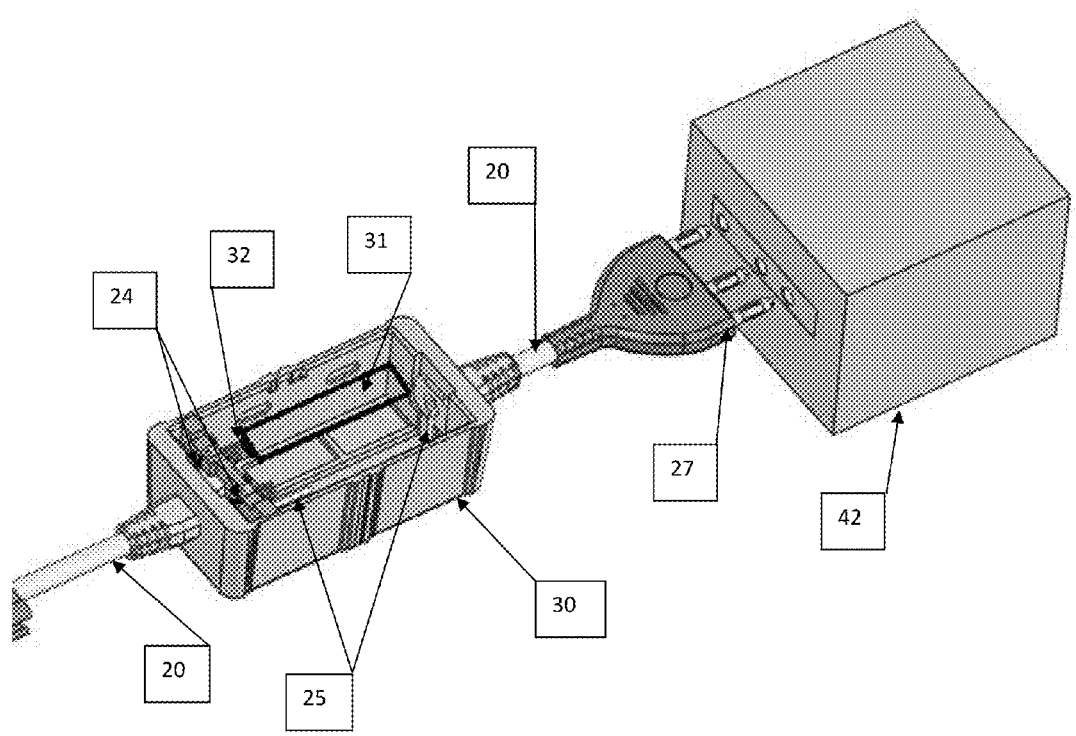
FIG. 3 illustrates a battery pack of the device of FIG. 1 with the external cable to be plugged into a generator.

FIG. 3 illustrates a battery pack (30) of the device (1) (not depicted) of FIG. 1 with the external cable (20) to be plugged into a generator (42). As illustrated, the battery pack (30) contains a battery (31), battery lead wires (24) transmitting electricity from battery contacts (32) to the powered element (2) (not depicted), and electrosurgical lead wires (25) transmitting a high-frequency signal from the generator (42) to the electrode (9) (not depicted) of the device (1) (not depicted). The external cable (20) contains a plug (27) to be inserted into the generator (42).

Figure 4:
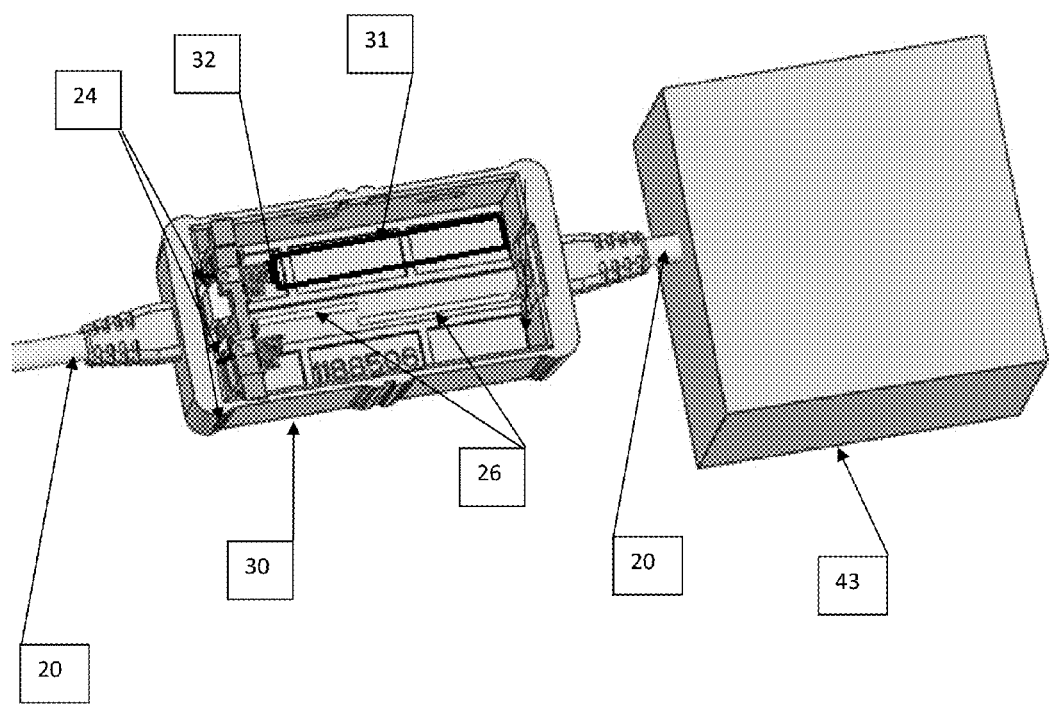
FIG. 4 illustrates a battery pack of the device of FIG. 2 with the external cable connected to an irrigation system.

FIG. 4 illustrates a battery pack (30) of the device (1) (not depicted) of FIG. 2 with the external cable (20) connected to an irrigation system (43). As illustrated, the battery pack (30) contains a battery (31), battery lead wires (24) transmitting electricity from battery contacts (32) to the powered element (2) (not depicted), and an irrigation line (26) transmitting a fluid from the irrigation system (43) to the device (1) (not depicted).

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. An article comprising:
    (i) a handheld device including:
        (a) a housing;
        (b) a powered element within the housing;
    (ii) a battery pack;
    (iii) an external cable having:
        (a) a first segment containing battery lead wires and an irrigation line; and
        (b) a second segment containing the irrigation line;
    wherein the handheld device is connected by the external cable to a functional system and the functional system is a console which houses an irrigation system;
    wherein the housing is connected to the battery pack by the first segment of the external cable;
    wherein the battery pack is attached to the functional system by the second segment of the external cable; and
    wherein the battery pack supplies power to the powered element.

2. The article according to claim 1, wherein the powered element is a motor.

3. The article according to claim 1, wherein the handheld device is an electrosurgical medical device.

4. The article according to claim 3, wherein the electrosurgical medical device is a debrider.

5. The article according to claim 4, wherein the electrosurgical medical device has at least one inner blade coupled to a motor.

6. The article according to claim 5, wherein the motor powers the at least one inner blade.

7. The article according to claim 1, wherein electricity is being transmitted via the battery lead wires to the powered element.

8. The article according to claim 1, wherein the powered element is a motor and the housing has a motor power switch.

9. The article according to claim 1, wherein the console is housed separate from the battery pack.

10. The article according to claim 9, wherein the irrigation line provides transmission of a fluid between the irrigation system to the housing.

11. The article according to claim 10, wherein the irrigation line is connected to an irrigation port in the housing.

12. The article of claim 11, wherein the fluid includes water, saline, aminoacetic acid, or antiseptic solution.

13. An article comprising:
    (i) a handheld device including:
        (a) a housing;

(b) a powered element within the housing;
(ii) a battery pack;
(iii) an external cable having:
  (a) a first segment containing battery lead wires and an irrigation line; and
  (b) a second segment containing the irrigation fine;
wherein the handheld device is connected by the external cable to a functional system and the functional system is a console which houses an Irrigation system and is separate from the battery pack;
wherein the housing is connected to the battery pack by the first segment of the external cable and the battery pack is attached to the functional system by the second segment of the external cable;
wherein the battery pack supplies power to the powered element; and
wherein the irrigation line is connected to an irrigation port in the housing.

14. The article according to claim 13, wherein the powered element is a motor.

15. The article according to claim 14, wherein the handheld device is an electrosurgical medical device.

16. The article according to claim 15, wherein the electrosurgical medical device is a debrider.

17. The article according to claim 16, wherein the electrosurgical medical device has at least one inner blade coupled to a motor and the motor powers the at least one inner blade.

18. The article according to claim 13, wherein electricity is being transmitted via the battery lead wires to the powered element.

19. The article according to claim 13, wherein the powered element is a motor and the housing has a motor power switch.

20. The article according to claim 13, wherein the irrigation line provides transmission of a fluid between the irrigation system to the housing.

* * * * *

UNITED STATES PATENT AND TRADEMARK OFFICE
CERTIFICATE OF CORRECTION

| | | |
|---|---|---|
| PATENT NO. | : 9,486,268 B2 | Page 1 of 1 |
| APPLICATION NO. | : 14/802109 | |
| DATED | : November 8, 2016 | |
| INVENTOR(S) | : Bennett et al. | |

It is certified that error appears in the above-identified patent and that said Letters Patent is hereby corrected as shown below:

In the Claims

Column 11, Line 6 delete "fine" and insert --line--

Signed and Sealed this
Twenty-eighth Day of February, 2017

Michelle K. Lee
*Director of the United States Patent and Trademark Office*